(12) United States Patent
Ikeda et al.

(10) Patent No.: US 9,207,073 B2
(45) Date of Patent: Dec. 8, 2015

(54) ACTIVE OBJECT DETECTION SENSOR

(71) Applicant: OPTEX CO., LTD., Shiga (JP)

(72) Inventors: Takayasu Ikeda, Otsu (JP); Kiyofumi Fukuda, Otsu (JP); Kenta Shimoji, Otsu (JP); Masayuki Shimazu, Otsu (JP); Takuya Maeda, Otsu (JP)

(73) Assignee: OPTEX CO., LTD., Shiga (JP)

( * ) Notice: Subject to any disclaimer, the term of this patent is extended or adjusted under 35 U.S.C. 154(b) by 0 days.

(21) Appl. No.: 14/555,969

(22) Filed: Nov. 28, 2014

(65) Prior Publication Data

US 2015/0153451 A1 Jun. 4, 2015

(30) Foreign Application Priority Data

Dec. 4, 2013 (JP) .................................. 2013-251411

(51) Int. Cl.
| | |
|---|---|
| *G01N 21/55* | (2014.01) |
| *G01C 3/00* | (2006.01) |
| *G01S 17/02* | (2006.01) |
| *G01S 17/46* | (2006.01) |
| *G01S 7/481* | (2006.01) |

(52) U.S. Cl.
CPC ........... *G01C 3/00* (2013.01); *G01N 21/55* (2013.01); *G01S 7/481* (2013.01); *G01S 17/026* (2013.01); *G01S 17/46* (2013.01)

(58) Field of Classification Search
CPC ............... G01N 2021/1793; G01N 2021/473; G01N 2021/6417
USPC ........................ 250/221, 342, 341, 559.4, 239
See application file for complete search history.

(56) References Cited

U.S. PATENT DOCUMENTS

| 4,310,756 A | * | 1/1982 | Sick et al. ..................... 250/221 |
| 5,137,350 A | | 8/1992 | Misawa et al. |
| 7,030,364 B2 | | 4/2006 | Matsuyama et al. |
| 2004/0169130 A1 | * | 9/2004 | Matsuyama et al. .......... 250/221 |

(Continued)

FOREIGN PATENT DOCUMENTS

| DE | 102011001387 A1 | 9/2012 |
| JP | 2004-170128 A | 6/2004 |

(Continued)

OTHER PUBLICATIONS

The extended European search report issued by the European Patent Office on May 20, 2015, which corresponds to European Patent Application No. 14195526.0-1812 and is related to U.S. Appl. No. 14/555,969.

*Primary Examiner* — Gregory J Toatley
*Assistant Examiner* — Iyabo S Alli
(74) *Attorney, Agent, or Firm* — Studebaker & Brackett PC

(57) ABSTRACT

An optical divider is disposed, in front of at least one of the transmitter and receiver elements, therebetween, and at least one of a transmission and reception side, and has a plurality of optical dividing pieces each having an optical deflection surface on which an angle of a detection ray is varied to a plurality of angles for dividing the detection ray toward a plurality of division areas. The optical deflection surface on at least one of the transmission and reception side is set to have a given angle, to assign at least one of the detection ray from the transmitter elements and toward the receiver elements, to a given division area, such that a combination of the transmitter and receiver elements forming one of the division areas is different from a combination of the transmitter and receiver elements forming another one of the division areas.

6 Claims, 11 Drawing Sheets

(56) References Cited

U.S. PATENT DOCUMENTS

2005/0035277 A1 2/2005 Matsuyama et al.
2010/0321676 A1 12/2010 Sasaki et al.

FOREIGN PATENT DOCUMENTS

| JP | 2009-115792 A | 5/2009 |
| JP | 2013-050368 A | 3/2013 |

* cited by examiner

ACTIVE OBJECT DETECTION SENSOR

CROSS REFERENCE TO THE RELATED APPLICATION

This application is based on and claims Convention priority to Japanese patent application No. 2013-251411, filed Dec. 4, 2013, the entire disclosure of which is herein incorporated by reference as a part of this application.

BACKGROUND OF THE INVENTION

1. Field of the Invention

The present invention relates to an active object detection sensor that transmits detection rays for object detection toward a detection area, and detects an object based on a reception signal generated when receiving detection rays reflected by the object.

2. Description of Related Art

To date, an active object detection sensor has been known which transmits detection rays, such as infrared rays or near infrared rays, for object detection, from a transmitter toward a detection area, causes a receiver that receives detection rays reflected by an object to generate a reception signal, and detects the object such as a human body when the reception signal is determined as having a level that exceeds a setting level.

As the active object detection sensor, the use is made of a sensor that forms a detection area divided into a plurality of division areas, to arrange plural columns of the division areas in a lateral direction, and arrange plural rows of the division areas in a longitudinal direction from a position close to the sensor toward a position distant from the sensor (for example, Japanese Laid-Open Patent Publication No. 2009-115792). The active object detection sensor is, for example, used for an automatic door sensor so as to detect an object for the automatic door.

FIG. 5A shows an example of a conventional sensor. The sensor 110 includes four phototransmitter (transmitter) elements 23 (elements EA to ED) and four photodetector (receiver) elements 24 (elements Ea to Ed), which are paired, respectively, so as to form four pairs, with lens bodies 25, 26 provided for between the phototransmitter elements 23 and the photodetector elements 24. For example, a light transmission area (transmission area) TA by the element EA and a light reception area (reception area) RA by the element Ea are overlaid or overlapped on each other to form a division area A1 of a first row or line, and a light transmission area TA by the element EB and a light reception area RA by the element Eb are overlaid or overlapped on each other to form a division area A2 of a second line. As shown in FIG. 5B, a detection area AA is formed by the four lines of the division areas A1 to A4, which lines are arranged in the longitudinal direction, from a position close to the sensor 110 toward a position distant from the sensor 110. In the example described herein, the division area A1 of the detection area AA is formed by combination of the element EA of the phototransmitter element 23 and the element Ea of the photodetector element 24, and the division area A2 is similarly formed by combination of the element EB and the element Eb. Thus, the respective combination of the phototransmitter element and the photodetector element which form each division area is different from a combination of the phototransmitter element and the photodetector element which form another division area, such that each combination is individually unique (hereinafter, referred to as a one-to-one relationship) and the same combination is not formed, thereby enabling each of the division areas A1 to A4 of the detection area AA to be uniquely identified. It is to be noted that a plurality of division areas are similarly formed in the lateral direction for each of the four lines of the division areas A1 to A4, which lateral division areas are not shown.

In order to improve safety and starting performance of an automatic door, intervals between the division areas need to be maintained constant while the detection area is extended in the longitudinal direction. Therefore, it is considered that the number of the phototransmitter elements and the photodetector elements are increased. FIG. 6A shows a sensor 120 in which the phototransmitter elements 33 and the photodetector elements 34 are paired respectively so as to form six pairs, that is, additionally including two pairs of the phototransmitter element 33 and the photodetector element 34 as compared to the sensor shown in FIG. 5A. As shown in FIG. 6B, the detection area AA having six rows or lines is formed by the six rows or lines of division areas A1 to A6 disposed in the longitudinal direction, from a position close to the sensor 120 toward a position distant from the sensor 120. Also in this example, combinations between the phototransmitter elements 33 (elements EA to EF) and the corresponding photodetector elements 34 (elements Ea to Ef) are provided in the one-to-one relationship, and each of the division areas A1 to A6 of the detection area AA can be uniquely identified.

However, in a case where the number of the transmitter elements and the receiver elements is increased, cost is increased correspondingly. Further, increase of the number of elements causes increase of the size of a device, and associated components need to be added, thereby further increasing cost.

It is known that, for addressing the above problem, a prism is disposed in front of the elements and the lens body to extend the detection area while the number of elements is reduced (for example, Japanese Laid-Open Patent Publication No. 2013-50368). In a sensor 130, as shown in FIG. 7, in a case where a prism is used, a detection ray transmitted from an element EA of a phototransmitter element 43 is divided in two directions by two prism surfaces of a prism 47, to form an area A and an area A' of a light transmission area (transmission area) TA, and a detection ray to be received by an element Ea of a photodetector element 44 is incident on a prism 48 from two directions from the area a and the area a' formed in a light reception area (reception area) RA, and the rays from the two directions are each transmitted toward the element Ea by two prism surfaces of the prism 48. For example, a first line is formed by the area A of the light transmission area TA and the area a of the light reception area RA, and a fourth is formed by the area A' of the light transmission area TA and the area a' of the light reception area RA, to form division areas A1 and A4 respectively. At this time, the area A and the area A', in the light transmission area TA, by the element EA of the phototransmitter element 43 cannot be distinguished from each other, and the area a and the area a', in the light reception area RA, by the element Ea of the photodetector element 44 cannot be distinguished from each other. Therefore, the division areas A1 of the first and A4 of the fourth are determined as the same area. The second and the fifth are similarly determined as being the same, and the third and the sixth are similarly determined as being the same. In a case where the aforementioned prism is used, the combination of the phototransmitter element 43 and the photodetector element 44 in each division area does not satisfy the one-to-one relationship, and the detection area cannot be uniquely identified.

SUMMARY OF THE INVENTION

The present invention has been made to solve the above problem and has an object to provide an active object detection sensor that is capable of uniquely identifying a detection area with ease in a case where the number of transmitter elements or receiver elements is reduced while the detection area is extended.

In order to attain the above object, an active object detection sensor of the present invention operates to form a detection area by a transmission area having a plurality of division areas and a reception area having a plurality of division areas being overlaid or overlapped on each other, and to detect an object in the detection area. The active object detection sensor includes: a plurality of transmitter elements each configured to transmit detection rays for object detection sequentially, to the transmission area; a plurality of receiver elements each configured to receive the detection ray reflected by the object from the reception area; and an optical divider disposed, in front of at least one of the transmitter elements and the receiver elements. The optical divider so disposed on at least one of a transmission side and a reception side, having a plurality of optical dividing pieces each having a plurality of optical deflection surfaces on which an angle of the detection ray is varied to a plurality of angles or directions for dividing the detection ray toward the plurality of division areas. The optical divider is configured such that the optical deflection surface in the optical dividing piece on at least one of the transmission side and the reception side is set to have a given angle, so as to assign at least one of the detection ray from the transmitter elements and the detection ray toward the receiver elements, to a given division area, such that a combination of the transmitter element and the receiver element forming one of the division areas is different from a combination of the transmitter element and the receiver element forming another one of the division areas.

In this configuration, the optical deflection surface in the optical dividing pieces on at least one of the transmission side and the reception side is set so as to have a given angle, and at least one of the detection ray on the transmission side and the reception side is assigned to a given division area. Therefore, the transmitter element forming each division area or the receiver element forming each division area can be optionally changed. Thus, combinations including the transmitter element forming each of the division area on the transmission side and the receiver element forming each of the division area on the reception side are made different from each other, and can be distinguished from each other. Thus, the plurality of transmitter elements for sequential transmission of the detection rays to each transmission area and the plurality of receiver elements for reception of the detection rays from each reception area can be uniquely combined in the one-to-one relationship. Therefore, the division area which can detect the object can be uniquely identified among the aforementioned combinations, and a detection area can be uniquely identified in a case where the number of transmitter elements or receiver elements is reduced while the detection area is extended by the division area being increased.

The optical divider may be provided on both of the transmission side and the reception side, and angles of the optical deflection surfaces in the optical dividing piece on the transmission side may be set so as to be different from each and/or angles of the optical deflection surfaces in the optical dividing piece on the reception side may be set so as to be different from each other. In this case, the number of the transmitter elements or the receiver elements can be made less than the number of the division areas, while each division area of the detection area can be uniquely identified.

Further, detection rays from the plurality of transmitter elements may be assigned to a given area among the division areas, so as to partially form the division area in which detection rays from the plurality of transmitter elements are overlaid on each other in the transmission area. Furthermore, detection rays toward the plurality of receiver elements may be assigned to a given area among the division areas, so as to partially form the division area in which detection rays toward the plurality of receiver elements are overlaid on each other in the reception area. Also in this case, the number of the transmitter elements or the receiver elements can be made less than the number of the division areas, while each division area of the detection area can be uniquely identified with ease.

Preferably, the optical divider is a prism having a prism surface that varies an angle of a traveling direction of the detection ray, to a plurality of angles. Therefore, the division areas can be easily formed. Further, the optical dividing piece may include two or three optical dividing surfaces, and may vary an angle of a traveling direction of the detection ray, to two or three angles. In this case, the number of the elements can be reduced.

Any combination of at least two constructions, disclosed in the appended claims and/or the specification and/or the accompanying drawings should be construed as included within the scope of the present invention. In particular, any combination of two or more of the appended claims should be equally construed as included within the scope of the present invention.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

DESCRIPTION OF EMBODIMENTS

Figure 1A:
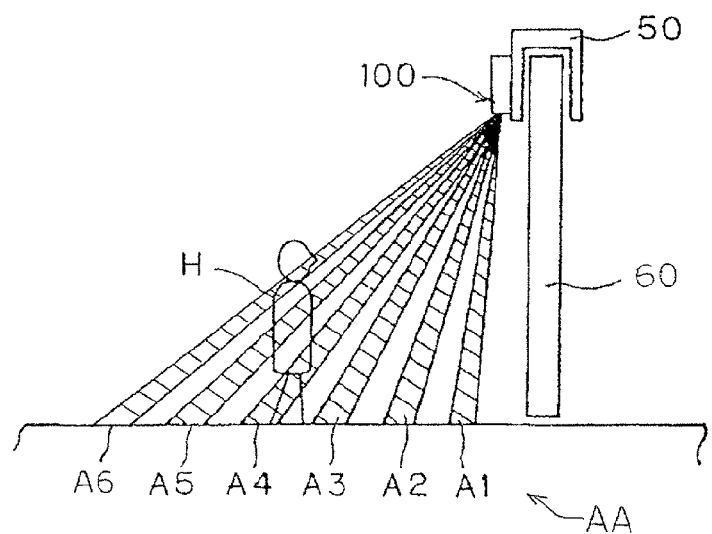
FIG. 1A illustrates a detection area as viewed from a sliding direction of an automatic door using an active object detection sensor for use in the automatic door according to one embodiment of the present invention.

Hereinafter, one embodiment of the present invention will be described with reference to the drawings. FIG. 1A illustrates a detection area AA, as viewed from a sliding direction of an automatic door 60, in the case of an active object detection sensor 100 for use in an automatic door being used for starting an opening/closing controller of the automatic door, according to one embodiment of the present invention. As shown in FIG. 1A, the active object detection sensor 100 is provided in a transom 50, and the detection area AA is formed by six rows or lines of division areas A1 to A6 in a longitudinal direction, from a position close to the sensor 100 toward a position distant from the sensor 100. In the detection area AA, an object such as a human body H is detected. A plurality of areas are also formed in a lateral direction for each of the division areas A1 to A6 of the six lines, which is not shown. The plurality of areas in the lateral direction may not be formed.

Figure 1B:
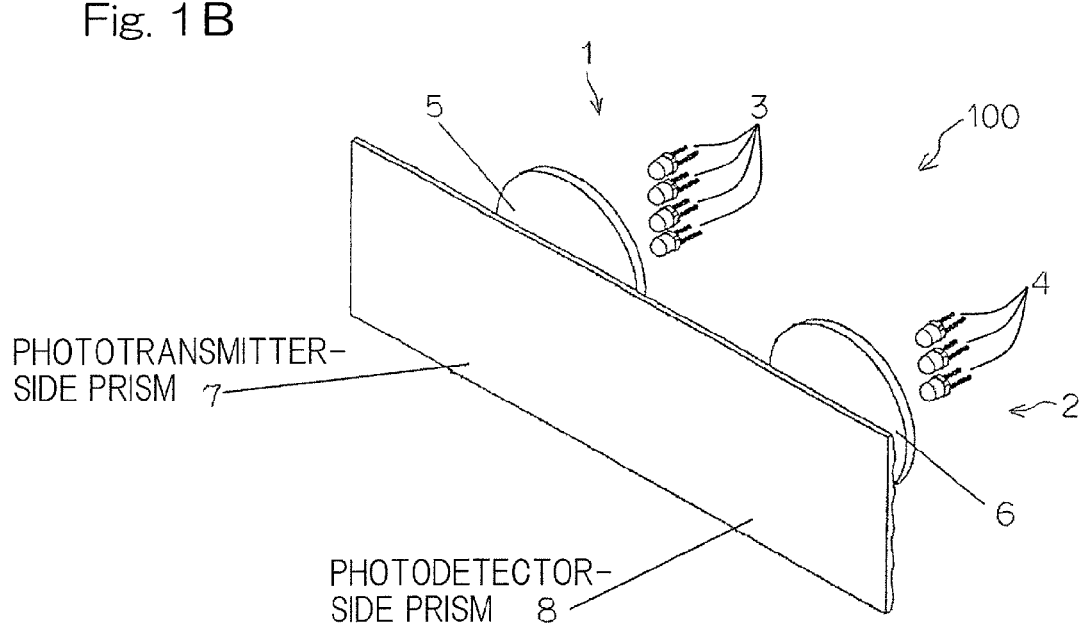
FIG. 1B is a schematic perspective view of the active object detection sensor.

As shown in FIG. 1B, the active object detection sensor 100 is, for example, an AIR (Active InfraRed detection) sensor, and includes: a phototransmitter 1 that transmits near infrared rays, as one kind of detection rays for object detection, toward the detection area AA described above; and a photodetector 2 that receives detection rays reflected by an object to generate a light reception signal.

The phototransmitter 1 includes: four phototransmitter elements 3 such as transmitter elements having infrared emitting diodes for transmitting near infrared rays as detection rays; a lens body 5 disposed in front of the phototransmitter elements 3; and a phototransmitter-side optical divider 7, such as a prism, disposed in front of the lens body 5. The photodetector 2 includes: three photodetector elements 4 such as receiver elements; a lens body 6 disposed in front of the photodetector elements 4; and a photodetector-side optical divider 8, such as a prism, disposed in front of the lens body 6. In FIG. 1B, the optical divider 7 and the optical divider 8 are integrated with each other. However, the optical divider 7 and the optical divider 8 may be separately provided. The lens bodies 5 and 6 operate to define or constrain the detection area AA. Each of the optical dividers 7 and 8 has peaks and troughs extending in a lateral or horizontal direction.

Figure 2A:
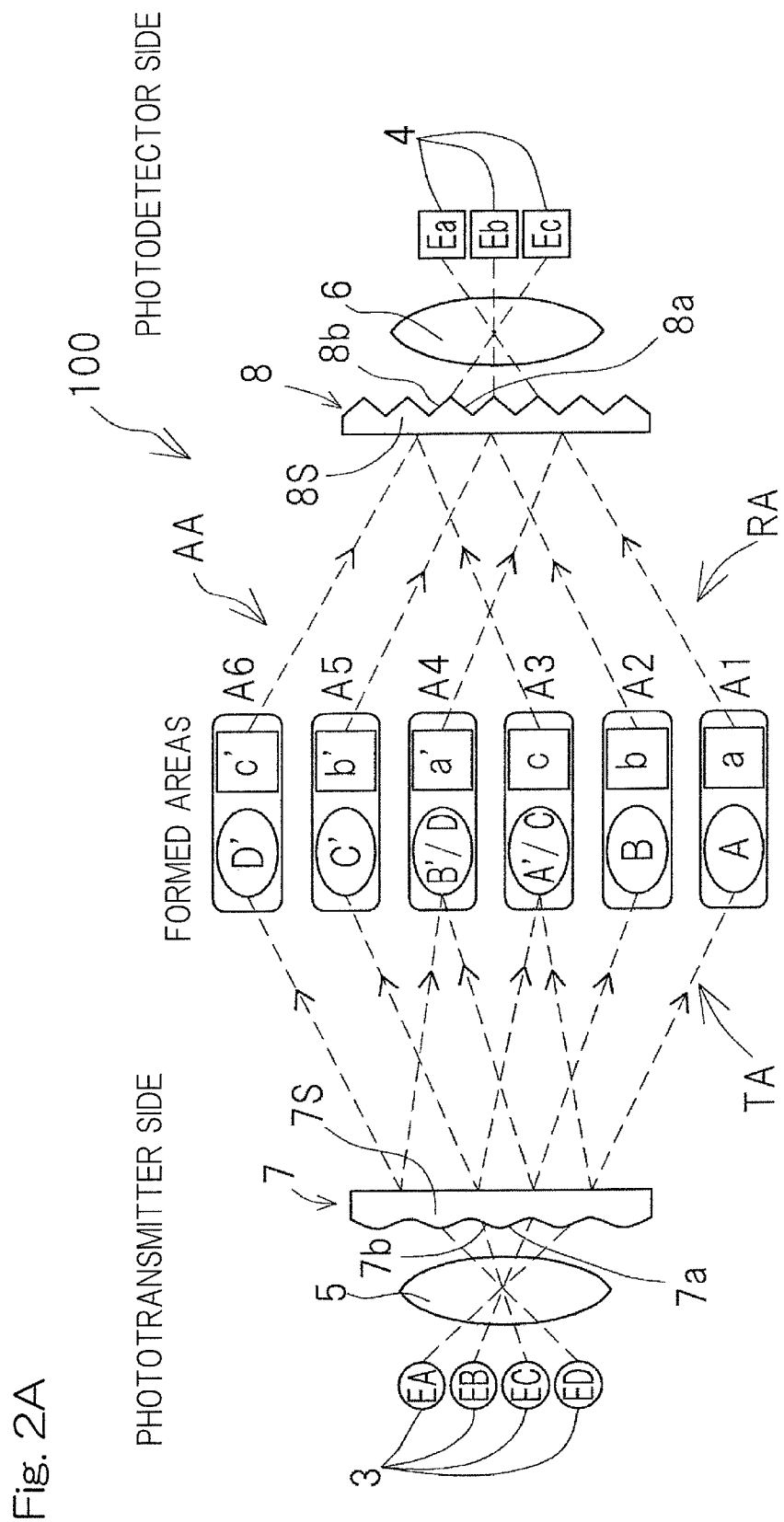
FIG. 2A is a schematic diagram illustrating a light transmission area by a phototransmitter element and a light reception area by a photodetector element.
Figure 2B:
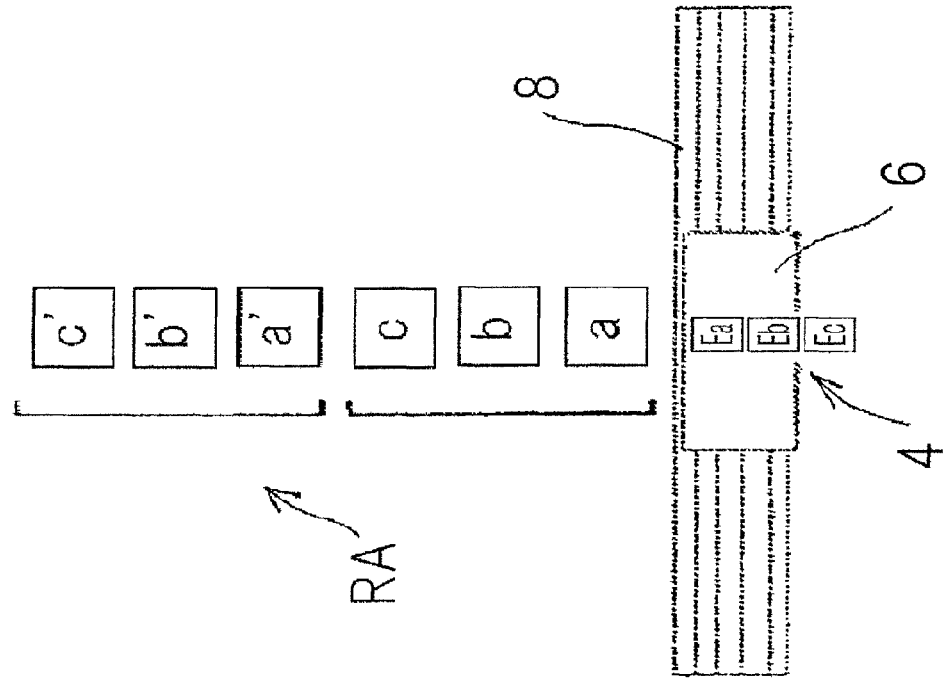
FIG. 2B is a schematic diagram illustrating a light transmission area by a phototransmitter element and a light reception area by a photodetector element.
Figure 2B:
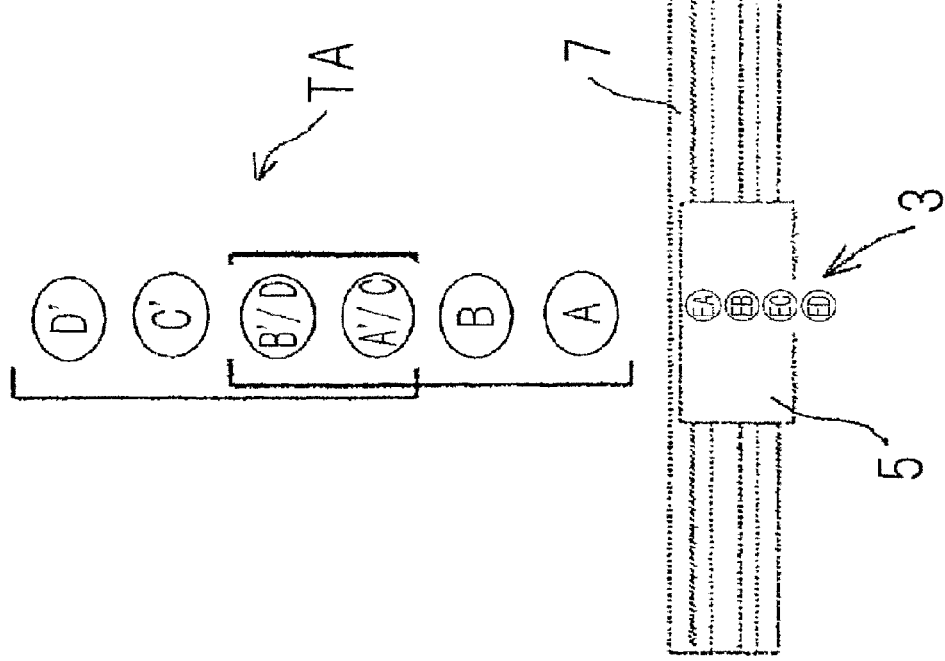
Figure 2C:
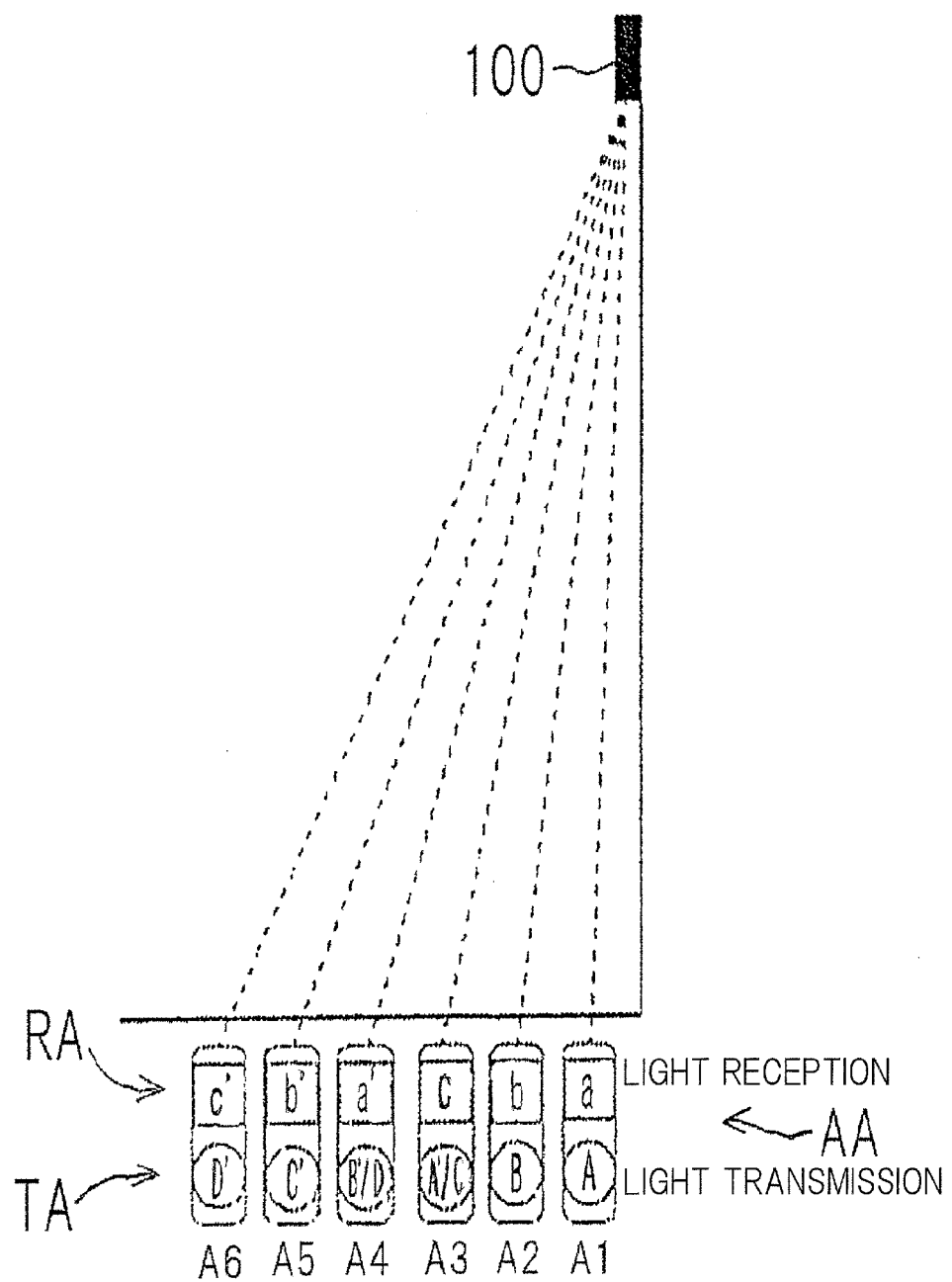
FIG. 2C is a side view of a detection area in which the light transmission area and the light reception area are overlaid on each other.

As shown in FIG. 2A and FIG. 2B, on the transmission side, that is, on the phototransmitter side, a light transmission area TA having six division areas is formed by the four phototransmitter elements 3, the lens body 5, and the phototransmitter-side prism 7. On the reception side, that is, on the photodetector side, a light reception area RA having six division areas is formed by the three photodetector elements 4, the lens body 6, and the photodetector-side prism 8. As shown in FIG. 2C, the light transmission area TA and the light reception area RA each having six division areas are overlaid on each other, thereby forming the detection area AA having the division areas A1 to A6.

As shown in FIG. 2A, the phototransmitter-side prism 7 has a plurality of optical dividing pieces (prism pieces) 7S having optical deflection surfaces (prism surfaces) 7a, 7b that vary a traveling direction or an angle thereof of a detection ray to a plurality of angles, for example, two angles, in order to divide the detection ray according to each division area, which the plurality of optical dividing pieces 7S are integrally formed. Each prism piece 7S has a predetermined angle at a prism peak (projecting portion) formed by the prism surfaces 7a, 7b, to divide the detection ray into, for example, two.

The photodetector-side prism 8 has a plurality of optical dividing pieces (prism pieces) 8S having optical deflection surfaces (prism surfaces) 8a, 8b that vary traveling direction angles (such as angles of incidence) of two aforementioned detection rays to a single identical angle (such as a refracted output angle) so as to collect the detection rays from the plurality of division areas, which the plurality of optical dividing pieces 8S are integrally formed. Each prism piece 8S has a predetermined angle at a prism peak (projecting portion) formed by the prism surfaces 8a, 8b, to change travelling directions of two detection rays (at this point, to equate the two travelling directions).

Further, in at least one combination between a combination of an angle of the optical deflection surface 7a and an angle of the optical deflection surface 7b of the phototransmitter-side prism 7, and a combination of an angle of the optical deflection surface 8a and an angle of the optical deflection surface 8b of the photodetector-side prism 8, the angles of the optical deflection surfaces (for example, the base angles of the triangle of the projecting portion) are different from each other. Here, the angle of the optical deflection surface 7a and the angle of the optical deflection surface 7b are different from each other, and/or the angle of the optical deflection surface 8a and the angle of the optical deflection surface 8b are different from each other. On at least one of the phototransmitter side detection ray and the photodetector side detection ray, an angle of a traveling direction (such as the angle of incidence for the prism 7) of the detection ray is changed based on an angle of a given optical deflection surface, to enable the detection ray to be varied and assigned to any division area.

In this example, both of the prisms 7, 8 have the given optical deflection surfaces. Alternatively, only the phototransmitter-side prism 7 may have the given optical deflection surface, or alternatively, only the photodetector-side prism 8 may have the given optical deflection surface. In this case, a detection ray can be assigned to any division area on each of the phototransmitter side and the photodetector side. The "given optical deflection surface" refers to an optical deflection surface at which an angle is set to such a given angle as to form the previously intended division areas.

A detection ray of the phototransmitter element 3 or the photodetector element 4 is assigned to any division area, thereby setting, in any manner, the phototransmitter element 3 or the photodetector element 4 to form each of the division areas. Thus, combinations of the phototransmitter element 3 and the photodetector element 4 that form the phototransmitter-side and photodetector-side division area, respectively, can be formed in any manner such that each of the combinations becomes different from another combination.

Hereinafter, an operation in the present embodiment will be specifically described. As shown in FIG. 2A, on the phototransmitter side, the light transmission area TA having six division areas is formed by the four phototransmitter elements 3 (elements EA, EB, EC, ED), the lens body 5, and the phototransmitter-side prism 7. On the photodetector side, the light reception area RA having six division areas is formed by the three photodetector elements 4 (elements Ea, Eb, Ec), the lens body 6, and the photodetector-side prism 8. The light transmission area TA and the light reception area RA are overlaid on each other, to form the division areas A1 to A6.

In this example, as shown in FIG. 2A, prism peaks of the transmission-side prism 7 and the reception-side prism 8 are formed such that each peak of the transmission-side prism 7 has an obtuse angle as compared to the peaks of the prism 8 since the phototransmitter-side prism is intended so as to be formed for assignment to given areas, and since an angle at which the transmission-side prism 7 diffuses a detection ray is less than an angle at which the reception-side prism 8 diffuses a detection ray due to the number of the phototransmitter elements 3 on the phototransmitter side being greater than the number of the photodetector elements 4 on the photodetector side.

As shown in FIG. 2B, in the light transmission area TA, division areas of A, B, A'/C, B'/D, C', D' are formed in order, respectively, from a position close to the sensor 100, that is, close to the phototransmitter element 3, and, in the light reception area RA, division areas of a, b, c, a', b', c' are formed in order, respectively, from a position close to the sensor 100, that is, close to the photodetector element 4. Here, the area A'/C represents one area, in the light transmission area TA, formed by a detection ray from the element EA of the phototransmitter element 3 and a detection ray from the element EC of the phototransmitter element 3.

As shown in FIG. 2C, in the detection area AA, the division area A1 is formed by the area A and the area a, the division area A2 is formed by the area B and the area b, the division area A3 is formed by the area A'/C and the area c, the division area A4 is formed by the area B'/D and the area a', the division area A5 is formed by the area C' and the area b', and the division area A6 is formed by the area D' and the area c'. Thus, each of the combinations including the phototransmitter element 3 and the photodetector element 4 are formed such that each combination can be different from each other in one-to-one relationship. Then, for example, by shifting positions of the assigned areas for the phototransmitter element 3 as compared to conventional art, even when the number of the phototransmitter elements 3 or the photodetector elements 4 is less than the number of the division areas, even where the areas formed by the photodetector elements 4 are positioned as in the conventional arts, each of the combinations including the phototransmitter element 3 and the photodetector element 4 can be formed to be different from each other.

Thus, each of the combinations including one or more phototransmitter elements for transmission to each light transmission area, and one or more photodetector elements for reception from each light reception area can be made different from each other so as to be each formed in the one-to-one relationship. That is, as compared to conventional arts, the number of the phototransmitter elements or the photodetector elements can be reduced, and a target division area can be uniquely detected without confusion caused by determining that one of the division areas is the same as another one of the division areas, to enable a division area that includes an object to be individually detected.

In this example, a detection ray is assigned to a given area of the division areas, and the division areas, such as the division areas A3 and A4, in which plural detection rays from the phototransmitter elements 3 are overlaid on each other are formed in a part of the light transmission area TA, that is, such division areas are partially formed in the light transmission area TA. Thus, the number of the phototransmitter elements 3 can be easily made less than the number of the division areas, that is, made less than six.

For example, in a case where the phototransmitter-side prism 7 for division into two is used, and a division area in which plural detection rays from the phototransmitter element 3 are overlaid on each other is formed in a part of the light transmission area TA as described above, the number of the phototransmitter elements 3 is set so as to be less than six that is the number of the lines of the division areas, and greater than three that is half of the number (six) of the lines, of the division areas. In this example, the number of the phototransmitter elements 3 is set to four.

In the above configuration, the automatic door apparatus shown in FIG. 1 determines whether or not a light reception signal that is individually inputted from the photodetector element 4 for each line has a level that exceeds a setting level. When the automatic door apparatus determines that the light reception signal has a level that exceeds the setting level, it outputs an object detection signal to a not-illustrated opening/closing controller of the automatic door 60. According to the object detection signal, the automatic door 60 is opened or closed.

Thus, in the present invention, an angle of a travelling direction of a detection ray on the phototransmitter (transmission) side and/or the photodetector (reception) side, is varied by the optical divider, and at least one of the detection ray on the transmission side and the reception side is assigned to a given division area, that is, to a given division area. Therefore, a combination of each transmitter element and each receiver element that form each division area can be varied in a given manner, and each combination including the transmitter element forming the division area on the transmission side and the receiver element forming the division areas on the reception side, can be made different from each other, and can be distinguished from each other. And the plurality of transmitter elements for sequential transmission of the detection rays to each transmission area and the plurality of receiver elements for reception of the detection rays from each reception area, can be uniquely combined in the one-to-one relationship. So, the division area which can detect the object H can be uniquely identified among the aforementioned combinations, and in a case where the number of the transmitter elements or the receiver elements is reduced while the detection area is extended, each detection area can be uniquely identified.

Hereinafter, variations 1 to 4 of the present invention will be described with reference to FIG. 3 and FIG. 4. Also in variations 1 to 4, while the number of the transmitter elements or the receiver elements is reduced, the detection area is extended, each detection area can be uniquely identified.

(Variation 1)

Figure 3A:
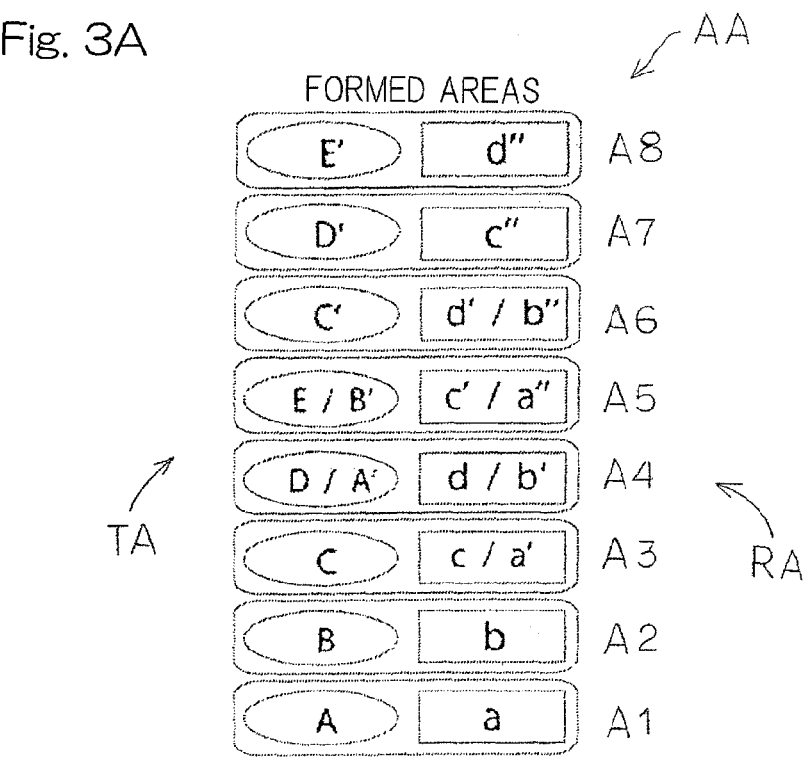
FIG. 3A illustrates a state where a light transmission area and a light reception area are overlaid on each other to form a detection area according to another example.

In FIG. 3A, on the phototransmitter side, eight division areas of the light transmission area TA are formed by five phototransmitter elements 3 (elements EA, EB, EC, ED, EE), and the prism 7 for division into two, and, on the photodetector side, eight division areas of the light reception area RA are formed by four photodetector elements 4 (elements Ea, Eb, Ec, Ed), and the prism 8 for division into three. A detection ray to the element Ea is divided in three directions so as to be assigned to a close area a, a distant area a", and an area a' between the areas a and a" by the prism 8 for division into three. Detection rays to the element Eb and Ec are similarly divided in three directions. In the detection area AA, a division area A1 is formed by an area A on the phototransmitter side and an area a on the photodetector side, a division area A2 is formed by an area B and an area b, a division area A3 is formed by an area C and an area c/a', a division area A4 is formed by an area D/A' and an area d/b', a division area A5 is formed by an area E/B' and an area c'/a", a division area A6 is formed by an area C' and an area d'/b", a division area A7 is formed by an area D' and an area c", and a division area A8 is formed by an area E' and an area d". In this example, both of division areas in each of which plural detection rays from the phototransmitter elements 3 are overlaid on each other, and division areas in each of which plural detection rays to the photodetector elements 4 are overlaid on each other, are partially formed.

(Variation 2)

Figure 3B:
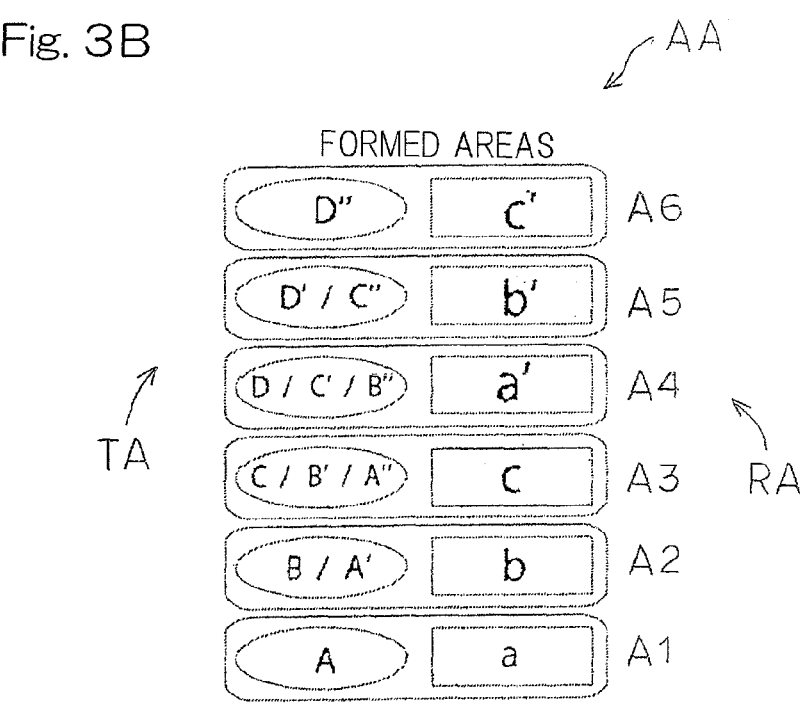
FIG. 3B illustrates a state where a light transmission area and a light reception area are overlaid on each other to form a detection area according to another example.

In FIG. 3B, on the phototransmitter side, six division areas of the light transmission area TA are formed by four phototransmitter elements 3 (elements EA, EB, EC, ED) and the prism 7 for division into three. For example, a detection ray from the element EA is divided in three directions, so as to be assigned to a close area A, a distant area A", and an area A' between the areas A and A", by the prism 7. On the photodetector side, six division areas of the light reception area RA are formed by three photodetector elements 4 (elements Ea, Eb, Ec), and the prism 8 for division into two. In the detection area AA, a division area A1 is formed by an area A on the phototransmitter side and an area a on the photodetector side, a division area A2 is formed by an area B/A' and an area b, a division area A3 is formed by an area C/B'/A" and an area c, a division area A4 is formed by an area D/C'/B" and an area a', a division area A5 is formed by an area D'/C" and an area b', and a division area A6 is formed by an area D" and an area c'. In this example, division areas in which plural detection rays from the phototransmitter elements 3 are overlaid on each other, are partially formed. For example, the area C/B'/A" represents one area, in the light transmission area TA, formed by a detection ray from the element EA of the phototransmitter element 3, a detection ray from the element EB thereof, and a detection ray from the element EC thereof.

(Variation 3)

Figure 4A:
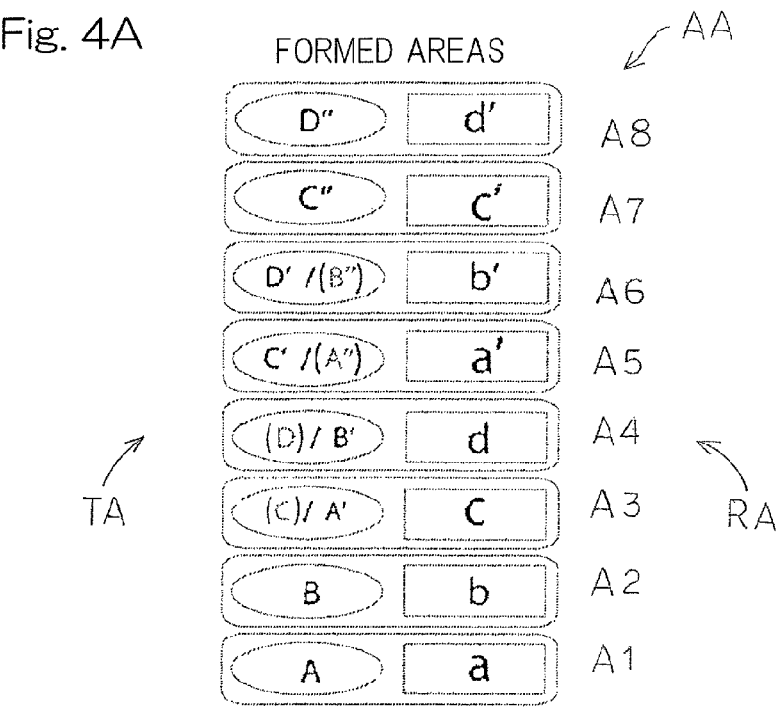
FIG. 4A illustrates a state where a light transmission area and a light reception area are overlaid on each other to form a detection area according to still another example.

As shown in FIG. 4A, on the phototransmitter side, eight division areas of the light transmission area TA are formed by four phototransmitter elements 3 (elements EA, EB, EC, ED), and the prism 7 for division into three, and, on the photodetector side, eight division areas of the light reception area RA are formed by four photodetector elements 4 (elements Ea, Eb, Ec, Ed), and the prism 8 for division into two. In the detection area AA, a division area A1 is formed by an area A on the phototransmitter side and an area a on the photodetector side, a division area A2 is formed by an area B and an area b, a division area A3 is formed by an area (C)/A' and an area c, a division area A4 is formed by an area (D)/B' and an area d, a division area A5 is formed by an area C'/(A") and an area a', a division area A6 is formed by an area D'/(B") and an area b', a division area A7 is formed by an area C" and an area c', and a division area A8 is formed by an area D" and an area d'. In this example, division areas in each of which plural detection rays from the phototransmitter elements 3 are overlaid on each other are partially formed. However, the areas in parentheses indicate not to be used for object detection. Therefore, areas in which detection rays are overlaid are not substantially formed.

(Variation 4)

Figure 4B:
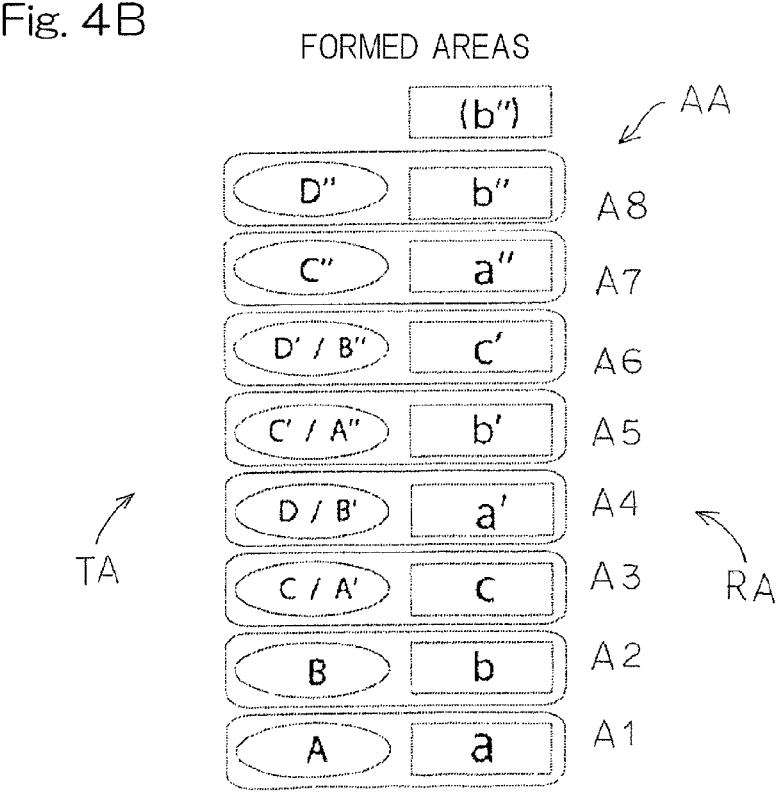
FIG. 4B illustrates a state where a light transmission area and a light reception area are overlaid on each other to form a detection area according to still another example.
Figure 5A:
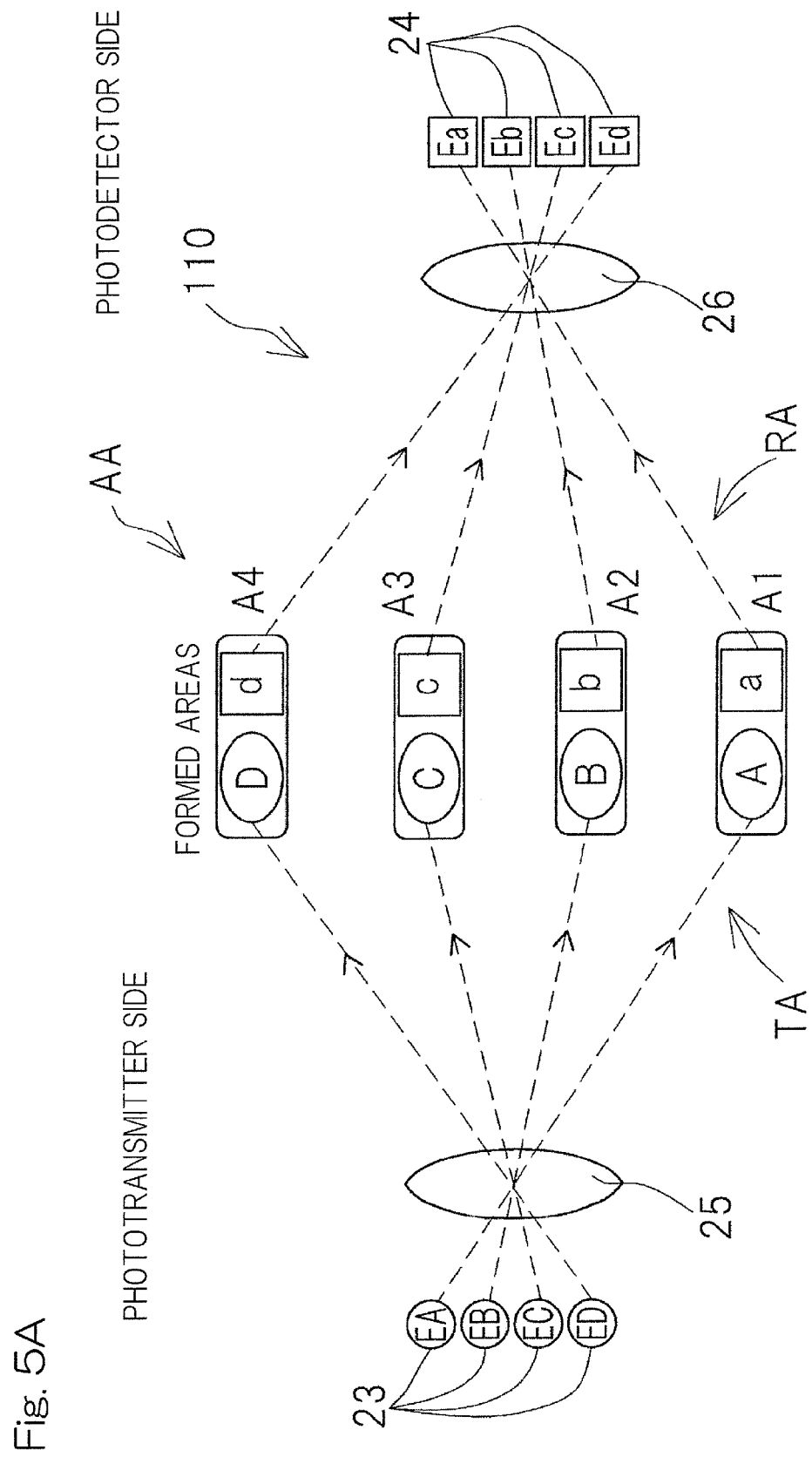
FIG. 5A is a schematic diagram illustrating a light transmission area by a phototransmitter element and a light reception area by a photodetector element in a conventional art.
Figure 5B:
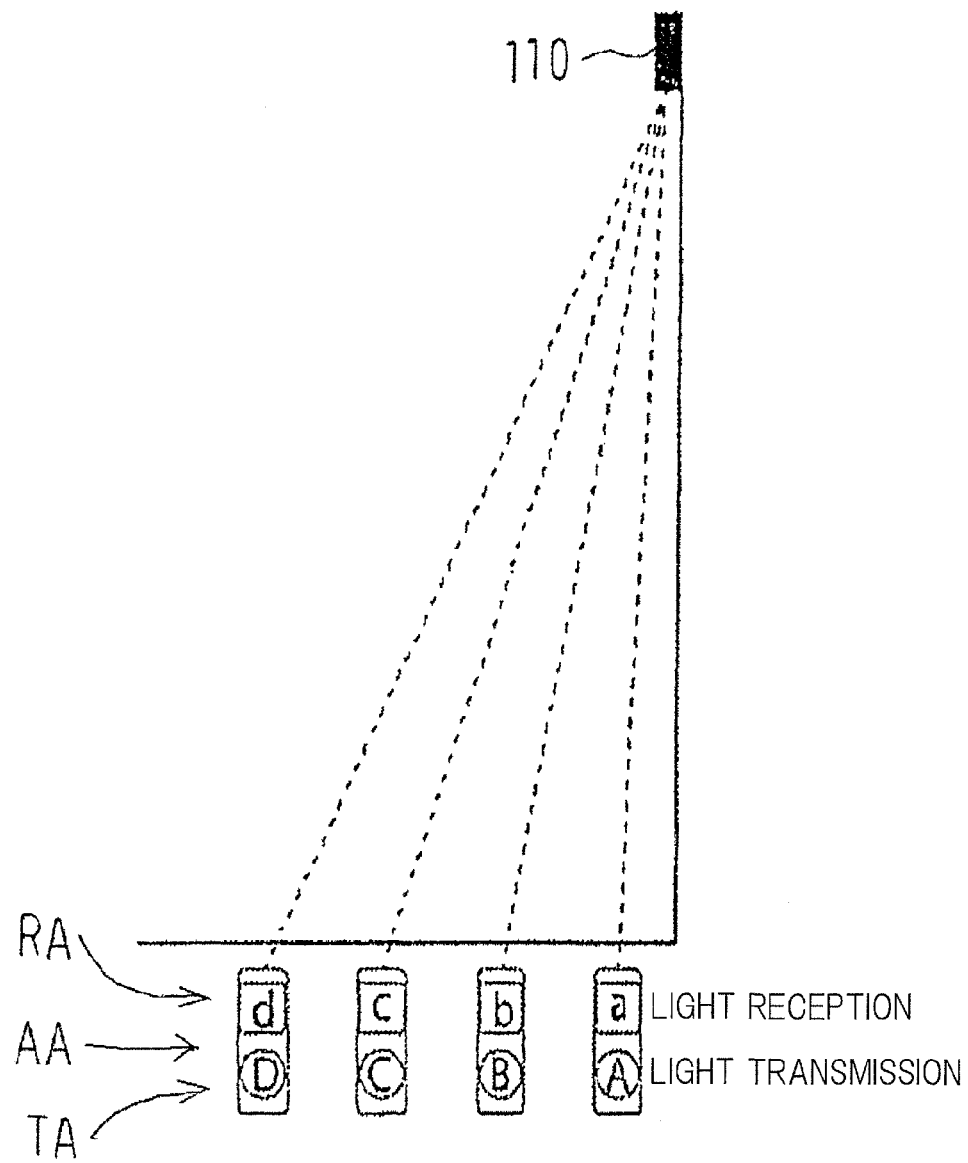
FIG. 5B is a side view of a detection area in which the light transmission area and the light reception area are overlaid on each other.
Figure 6A:
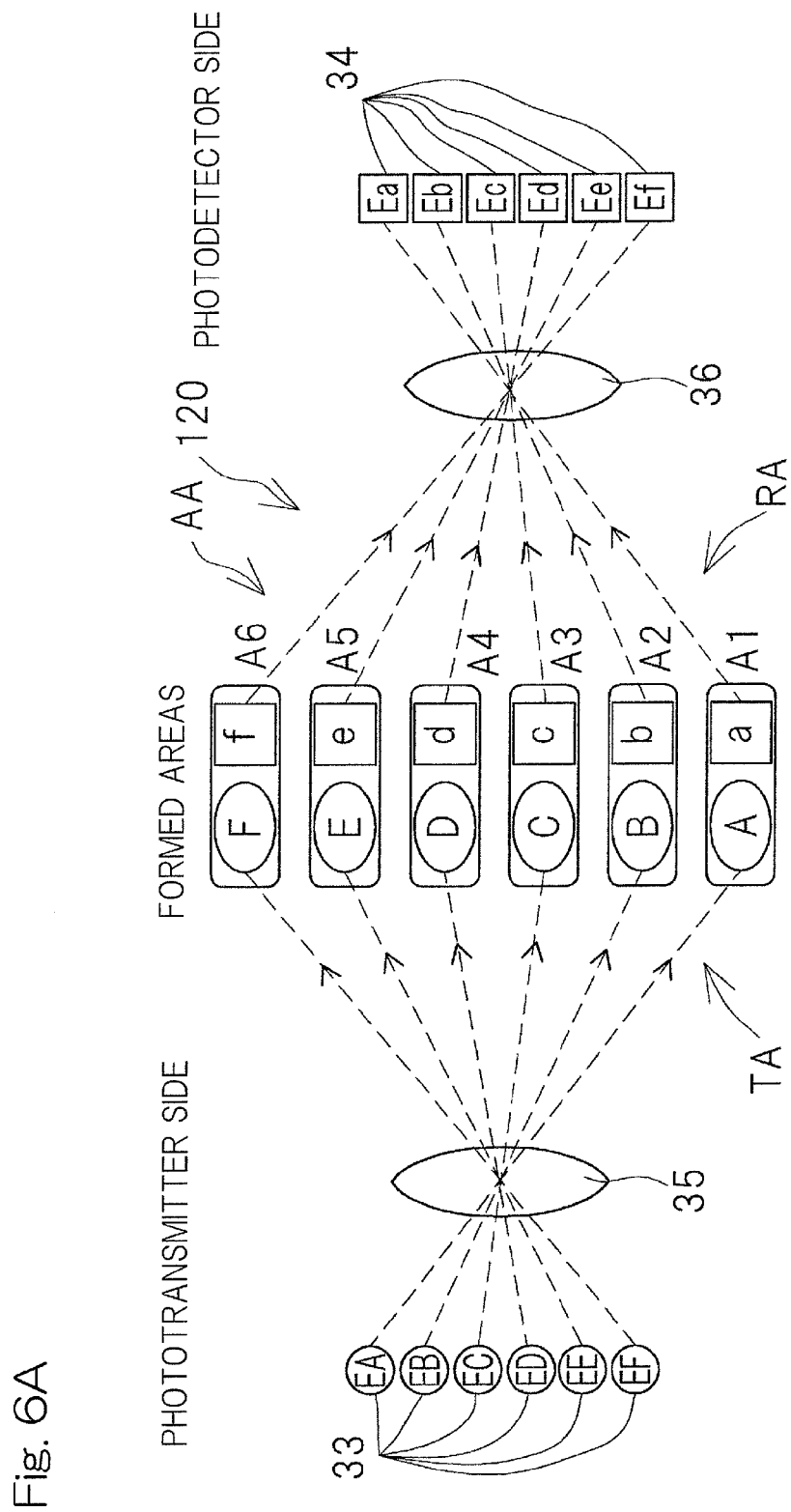
FIG. 6A is a schematic diagram illustrating a light transmission area by a phototransmitter element and a light reception area by a photodetector element in a conventional art.
Figure 6B:
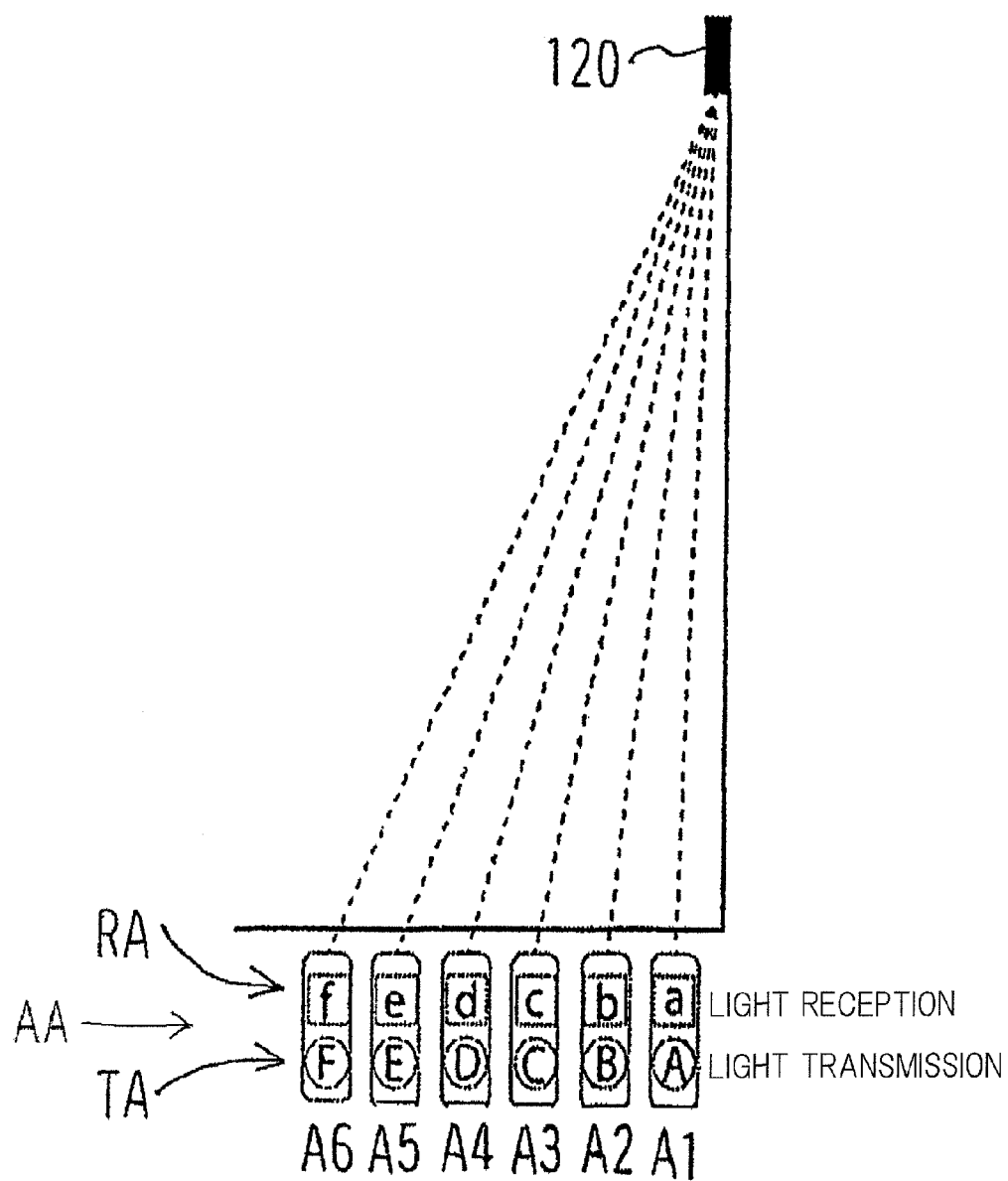
FIG. 6B is a side view of a detection area in which the light transmission area and the light reception area are overlaid on each other.
Figure 7:
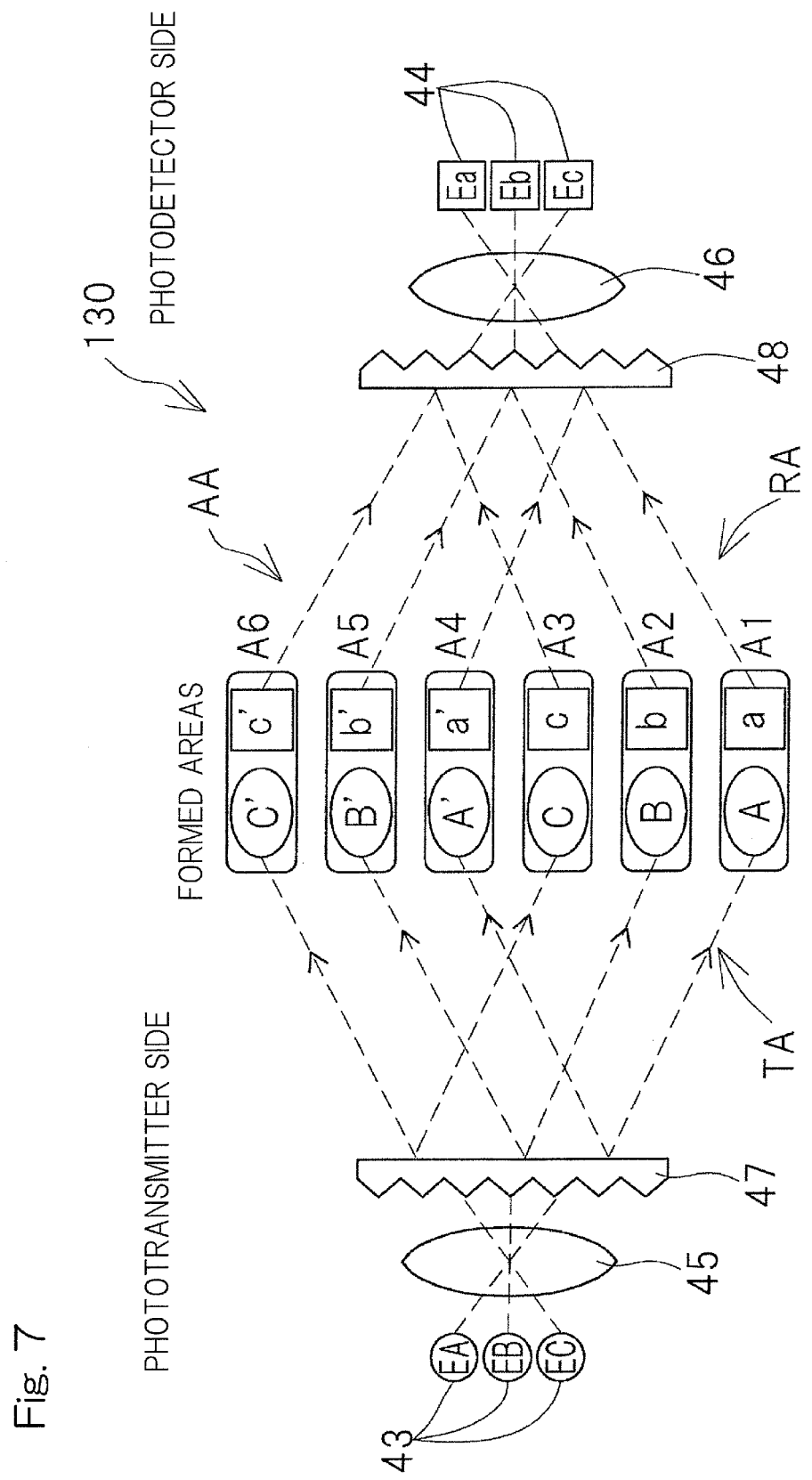
FIG. 7 is a schematic diagram illustrating a light transmission area by a phototransmitter element and a light reception area by a photodetector element in the case of a prism in a conventional art being used.

As shown in FIG. 4B, on the phototransmitter side, eight division areas of the light transmission area TA are formed by four phototransmitter elements 3 (elements EA, EB, EC, ED) and the prism 7 for division into three, and, on the photodetector side, eight division areas of the light reception area RA are formed by three photodetector elements 4 (elements Ea, Eb, Ec) and the prism 8 for division into three. In the detection area AA, a division area A1 is formed by an area A on the phototransmitter side and an area a on the photodetector side, a division area A2 is formed by an area B and an area b, a division area A3 is formed by an area C/A' and an area c, a division area A4 is formed by an area D/B' and an area a', a division area A5 is formed by an area C'/A" and an area b', a division area A6 is formed by an area D'/B" and an area c', a division area A7 is formed by an area C" and an area a", and a division area A8 is formed by an area D" and an area b". An area represented by (b") is not used. In this example, division areas in each of which plural detection rays from the phototransmitter elements 3 are overlaid on each other are partially formed.

In each embodiment, near infrared rays are used as detection rays. However, detection rays are not limited to near infrared rays. For example, visible light, infrared rays, microwaves, or laser light may be used.

In each embodiment, a plurality of division areas are formed in the longitudinal direction from a position close to a sensor toward a position distant from the sensor. However, a plurality of the division areas may be formed in the lateral direction.

In each embodiment, a prism is used as an optical divider for forming a plurality of areas according to a detection ray for one element. However, the optical divider is not limited to a prism. For example, a mirror having a plurality of optical deflection surfaces (mirror surfaces) may be used.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

REFERENCE NUMERALS

1 . . . phototransmitter
2 . . . photodetector
3 . . . phototransmitter (transmitter) element
4 . . . photodetector (receiver) element
5, 6 . . . lens body
7 . . . phototransmitter-side optical divider (prism)
7S . . . optical dividing piece (prism piece)
7a, 7b . . . optical deflection surface (prism surface)
8 . . . photodetector-side optical divider (prism)
8S . . . optical dividing piece (prism piece)
8a, 8b . . . optical deflection surface (prism surface)
60 . . . automatic door
100 . . . active object detection sensor
AA . . . detection area
A1 to A6 . . . division area
TA . . . light transmission area (transmission area)
RA . . . light reception area (reception area)

What is claimed is:

1. An active object detection sensor that operates to form a detection area by a transmission area having a plurality of division areas and a reception area having a plurality of division areas being overlaid on each other, and to detect an object in the detection area, the active object detection sensor comprising:

a plurality of transmitter elements each configured to transmit detection rays for object detection sequentially, to the transmission area;

a plurality of receiver elements each configured to receive the detection ray reflected by the object from the reception area; and an optical divider disposed, in front of at least one of the transmitter elements and the receiver elements, wherein the optical divider, so disposed on at least one of a transmission side and a reception side, has a plurality of optical dividing pieces each having a plurality of optical deflection surfaces on which an angle of the detection ray is varied to a plurality of angles for dividing the detection ray toward the plurality of division areas, the optical deflection surface in the optical dividing pieces on at least one of the transmission side and the reception side being set to have a given angle, so as to assign at least one of the detection ray from the transmitter elements and the detection ray toward the receiver elements, to a given division area, such that a combination of the transmitter elements and the receiver elements forming one of the division areas is different from a combination of the transmitter elements and the receiver elements forming another one of the division areas.

2. The active object detection sensor as claimed in claim 1, wherein the optical divider is provided on both of the transmission side and the reception side, and angles of the optical deflection surfaces in the optical dividing piece on the transmission side are set so as to be different from each other and/or angles of the optical deflection surfaces in the optical dividing piece on the reception side are set so as to be different from each other.

3. The active object detection sensor as claimed in claim 1, wherein detection rays from the plurality of transmitter elements are assigned to a given area among the division areas, so as to partially form the division area in which detection rays from the plurality of transmitter elements are overlaid on each other in the transmission area.

4. The active object detection sensor as claimed in claim 1, wherein detection rays toward the plurality of receiver elements are assigned to a given area among the division areas, so as to partially form the division area in which detection rays toward the plurality of receiver elements are overlaid on each other in the reception area.

5. The active object detection sensor as claimed in claim 1, wherein the optical divider is a prism having a prism surface that varies an angle of a traveling direction of the detection ray, to a plurality of angles.

6. The active object detection sensor as claimed in claim 1, wherein the optical dividing piece includes two or three optical dividing surfaces, and varies an angle of a traveling direction of the detection ray, to two or three angles.

* * * * *